United States Patent [19]

Gohno et al.

[11] Patent Number: 5,521,955
[45] Date of Patent: May 28, 1996

[54] METHOD FOR QUANTITATIVELY DETERMINING BONE MINERAL MASS BY CT SYSTEM

[75] Inventors: Makoto Gohno; Tetsuya Horiuchi, both of Tokyo, Japan

[73] Assignee: GE Yokogawa Medical Systems, Limited, Tokyo, Japan

[21] Appl. No.: 343,510

[22] PCT Filed: May 25, 1993

[86] PCT No.: PCT/JP93/00698

§ 371 Date: Nov. 21, 1994

§ 102(e) Date: Nov. 21, 1994

[87] PCT Pub. No.: WO93/24055

PCT Pub. Date: Dec. 9, 1993

[30] Foreign Application Priority Data

May 29, 1992 [JP] Japan .................................. 4-139404

[51] Int. Cl.$^6$ .................................................. A61B 6/03
[52] U.S. Cl. ......................... 378/18; 378/56; 364/413.02
[58] Field of Search ............................... 378/18, 207, 56, 378/901; 364/413.02

[56] References Cited

U.S. PATENT DOCUMENTS 4,233,507  11/1980  Volz ............................................ 378/18
4,985,906  1/1991  Arnold ........................................ 378/18
5,034,969  7/1991  Ozaki ......................................... 378/18
5,222,021  6/1993  Feldman et al. ..................... 364/413.14
5,335,260  8/1994  Arnold ...................................... 378/207

*Primary Examiner*—David P. Porta
*Assistant Examiner*—David Vernon Bruce
*Attorney, Agent, or Firm*—Moonray Kojima

[57] ABSTRACT

A method for quantitatively determining bone mineral mass by a CT system, comprising scanning an objective region together with a plurality of samples produced by mixing a water equivalent material with various ratios of a standard material equivalent to bone mineral mass and determining the bone mineral density of the objective region with reference to the CT numbers of the samples, wherein a plurality of samples are scanned together with the objective region at one or multiple levels of tube voltage and a corrected CT number of each sample is calculated by substituting the CT number of each of the samples with the CT number of blood or a standard material equivalent to blood. By scanning at a single level of tube voltage, bone mineral density is determined, on the basis of the CT number of the objective region and with reference to the corrected CT numbers. On the other hand, by scanning at multiple levels of tube voltage, bone mineral density is determined on the basis of the CT number of the objective region and with reference to the corrected CT numbers while excluding the effect of fat. In the foregoing manner errors due to blood and fat are corrected.

4 Claims, 6 Drawing Sheets

Fig.3
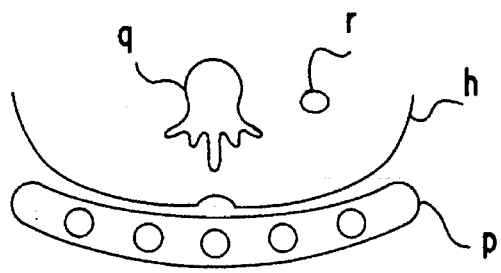
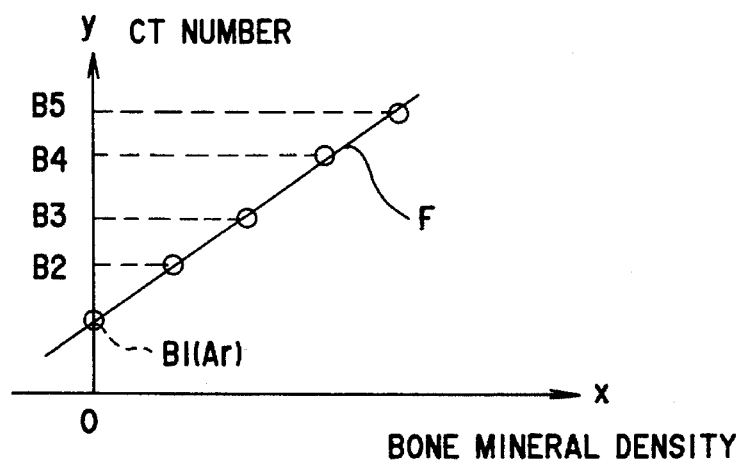
Fig.4
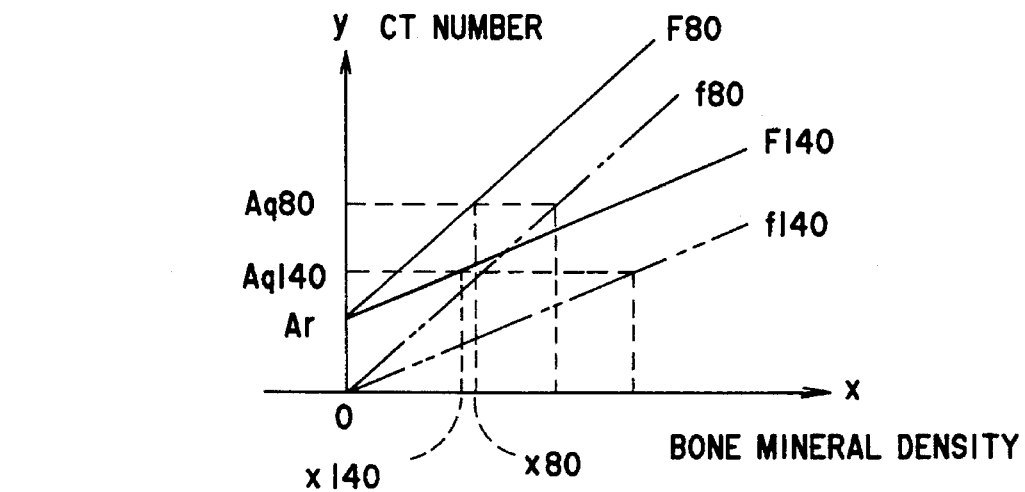
Fig.5

METHOD FOR QUANTITATIVELY DETERMINING BONE MINERAL MASS BY CT SYSTEM

TECHNICAL FIELD

The present invention relates to a method for quantitatively determining bone mineral mass with a CT scanner. More particularly, the present invention relates to a method for quantitatively determining bone mineral mass by a CT system, comprising scanning an objective region together with plural samples produced by mixing a water equivalent material (a material having the same X-ray transmission rate as that of water) with various ratios of a standard material equivalent to bone mineral mass (a material having the same X-ray transmission rate as that of bone mineral mass) and determining the bone mineral density (BMD) of the objective region with reference to the CT numbers of the plural samples with various densities of the standard material equivalent to bone mineral mass.

BACKGROUND ART

Quantitative determination of bone mineral mass is used for diagnosis of osteoporosis and the like.

Quantitative determination of bone mineral mass in bone marrow as an objective region will be outlined hereinbelow.

As shown in FIG. 8, phantom P is placed below the waist of a subject. Then, scanning with a CT scanner yields the image data of the cross section including the bone marrow (for example, the third lumbar vertebrae) and the phantom P. Herein, the phantom P contains plural sample rods S1, S2, ..., produced by mixing a water equivalent material having the same X-ray transmission rate as that of water with various ratios of a standard material equivalent to bone mineral mass which has the same X-ray transmission rate as that of bone mineral mass.

Then, detecting CT numbers A1, A2, ... of the sample rods S1, S2, ... in the cross sectional image data, a linear regression "e" representing the relation between the CT number and the bone mineral density of the standard material equivalent to bone mineral mass as shown in FIG. 9 is calculated on the basis of the CT numbers A1, A2, ... and the densities of the standard material equivalent to bone mineral mass in the sample rods S1, S2, ... The X axis represents bone mineral density, while the y axis represents CT number.

Then, detecting the CT number of the bone marrow as the objective region in the cross sectional image date, the bone mineral density of the bone marrow is calculated on the basis of the detected CT number and the linear regression "e".

As illustrated in FIG. 10, however, the bone mineral density calculated on the basis of the linear regression "e" is sometimes inconsistent with the true value.

For example, a linear regression generated from scanning at an X-ray tube voltage of 80 kV is designated "e80"; the CT number of bone marrow is designated "Aq80"; and the bone mineral density derived from these is designated "x80". Alternatively, a linear regression generated from scanning at an X-ray tube voltage of 140 kV is designated "e140"; the CT number of bone marrow is designated "Aq140"; and the bone mineral density derived from these is designated "x140". Then, the bone mineral density "xt", which should be constant irrespective to the difference in tube voltage, is actually not constant as illustrated in x80<x140. Such results may possibly be due to some error factors. Therefore, since the decrease in CT number due to fat may be one of such error factors, the shift of measured bone mineral density from the true bone mineral density "xt" at each tube voltage is calculated while the decrease in CT number due to fat is designated "af". Then, x80 should be more than x140, as shown in FIG. 11, which is not consistent with the above results shown in FIG. 10. Thus, such calculation of bone mineral density as shown in FIG. 10 may possibly contain a certain error factor other than fat, but the factor has not been identified yet. Hence, the error factor due to fat has not been excluded either.

DISCLOSURE OF INVENTION

Thus, the objective of the present invention is to provide a modified method for quantitatively determining bone mineral mass to obtain more accurate bone mineral density.

A method for quantitatively determining bone mineral mass by a CT system in accordance with the present invention comprises scanning an objective region together with plural samples produced by mixing a water equivalent material (a material having the same X-ray transmission rate as that of water) with various ratios of a standard material equivalent to bone mineral mass (a material having the same X-ray transmission rate as that of bone mineral mass) and determining the bone mineral density of the objective region with reference to the CT numbers of the plural samples with various densities of the standard material equivalent to bone mineral mass, wherein the corrected CT number of each of the samples with various densities of the standard material equivalent to bone mineral mass is calculated by substituting the CT number derived from the water equivalent material and contained in the CT number of each of the samples with the CT number of blood or a standard material equivalent to blood (a standard material having the same X-ray transmission rate as that of blood) in the cross sectional image data generated from such scanning and determining the bone mineral density of the objective region on the basis of the corrected CT numbers of the individual samples.

The other method for quantitatively determining bone mineral mass by a CT system in accordance with the present invention comprises effecting multiple scanning at different levels of X-ray tube voltage, calculating corrected CT number of each of samples with various densities of a standard material equivalent to bone mineral mass at each scanning by substituting the CT number derived from a water equivalent material and contained in the CT number of each of the samples with the CT number of blood or a standard material equivalent to blood in the cross sectional image data generated from such scanning, determining the relation at each scanning between the corrected CT number and the bone mineral density of the standard material equivalent to bone mineral mass, and determining the bone mineral density of an objective region while correcting the shift of the CT number in the objective region by using the relation between them together with the corrected CT number of each of the samples.

The primary component in soft tissues in human bodies and the like is blood, which is the case with bone marrow as the objective region for quantitative determination of bone mineral mass. Therefore, according to the method for quantitatively determining bone mineral mass by a CT system in accordance with the present invention, the corrected CT number of each of plural samples with various densities of a standard material equivalent to bone mineral mass is calculated by substituting the CT number derived from a water equivalent material and contained in the Ct number of each of the samples with the CT number of blood or a standard material equivalent to blood in the cross sectional image data generated from scanning.

Because the corrected CT number of each of the samples is a value corrected for blood or a standard material equivalent to blood so as to more accurately reproduce a soft tissue as the objective region, more accurate bone mineral density can be obtained by determining the bone mineral density of the objective region based on the corrected CT number of each of the samples.

Furthermore, such corrected CT numbers are obtained at plural levels of tube voltage, to determine the bone mineral density of the objective region while correcting the shift in CT number due to fat and the like. Therefore, a more accurate value of bone mineral density is yielded.

BRIEF DESCRIPTION OF DRAWINGS

FIG. 3 is an illustration depicting a cross sectional image in accordance with the present invention;

FIG. 4 is an illustration depicting a linear regression in accordance with the present invention;

FIG. 5 is an illustration depicting linear regressions in accordance with the present invention;

BEST MODE FOR CARRYING OUT THE INVENTION

The present invention will now be described in using examples shown in the figures, but the inventions not limited to the examples.

Figure 7:
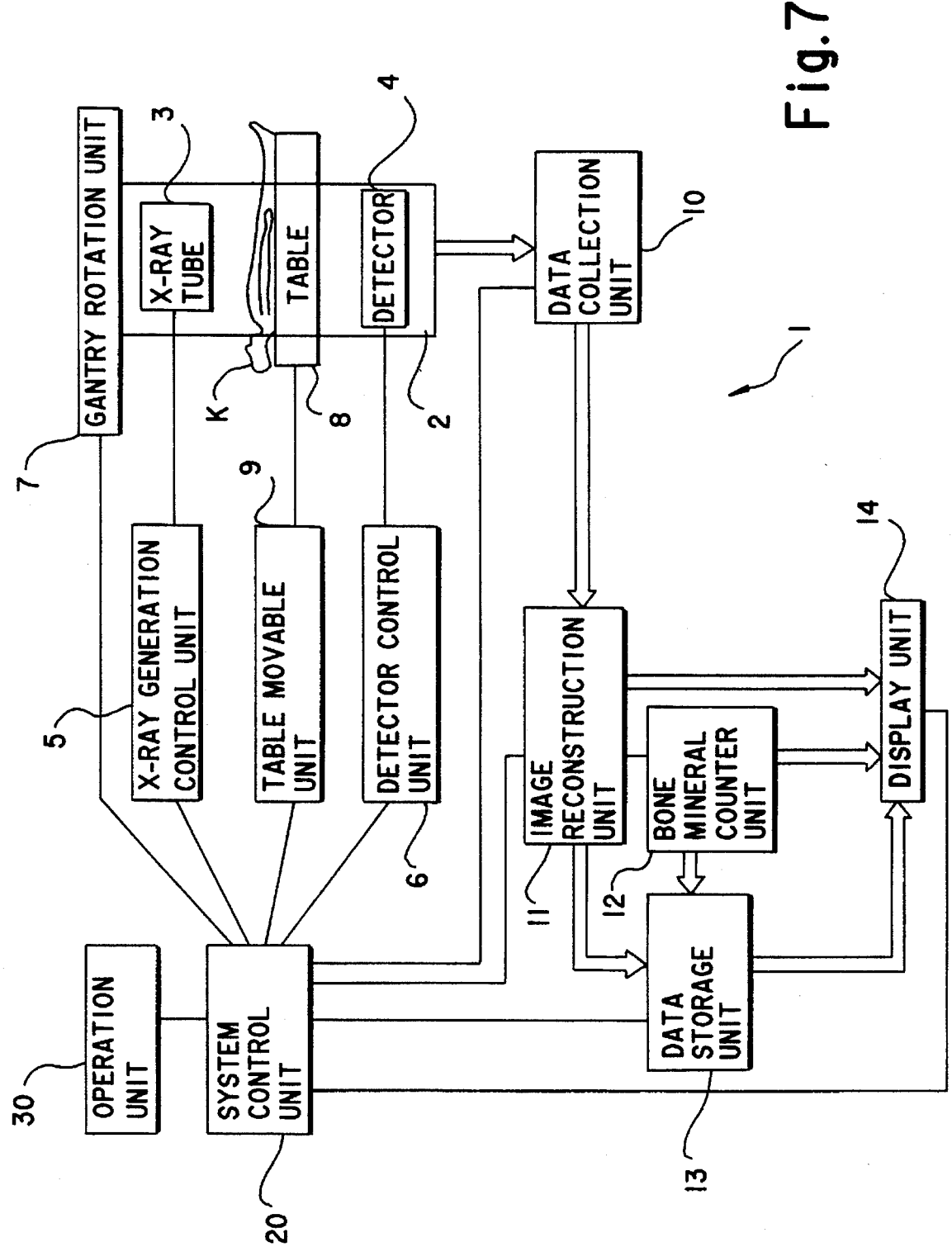
FIG. 7 is a block diagram depicting a system for carrying out the method for quantitatively determining bone mineral mass in accordance with the present invention.
Figure 8:
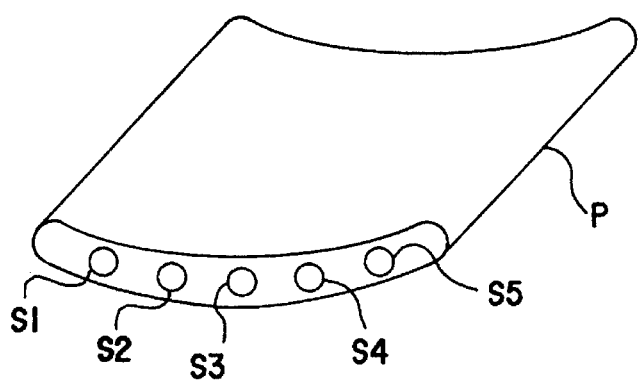
FIG. 8 is an illustration representing a phantom to be used for quantitatively measuring bone mineral mass in accordance with the present invention.

FIG. 7 is a block diagram depicting CT system 1 for carrying out the method for quantitatively determining bone mineral mass in one example in accordance with the present invention. X-ray tube 3 and detector 4, both placed in gantry 2, are integrally rotated with gantry rotation system 7. The detector 4 detects the intensity of X-ray transmitted through subject K. X-ray generation control circuit 5 is connected to x-ray tube 3, to control X-ray generation and the cessation thereof and to control the tube voltage of X-ray tube 3. Detector control circuit 6 controls the timing to operate detector 4. Table 8 is for receiving thereon the subject K, and is linearly movable with table movable unit 9. Data collection unit 10 collects projection data from the detector 4. Image reconstitution unit 11 reconstitutes an image based on the projection data from the data collection unit 10, to output cross sectional image data. On the basis of the cross sectional image data obtained by the image reconstitution unit 11, bone mineral counter unit 12 is for carrying out the procedures of the present invention as described hereinafter to count the bone mineral density of an objective region. Data storage unit 13 stores the cross sectional image data from the image reconstitution unit 11 together with the data counted with the bone mineral counter unit 12. Display unit 14 displays a cross sectional image on the basis of the cross sectional image data from the image reconstitution unit 11, as well as the bone mineral density of the objective region on the basis of the data counted with the bone mineral counter unit 12. System control unit 20 transfers and receives necessary signals to and from X-ray generation control circuit 5, detector control circuit 6, gantry rotation unit 7, table movable unit 9, data collection unit 10, image reconstitution unit 11, bone mineral count unit 12, data storage unit 13, and display unit 14. Operation unit 30 is for an operator to input commands and the like.

Figure 2:
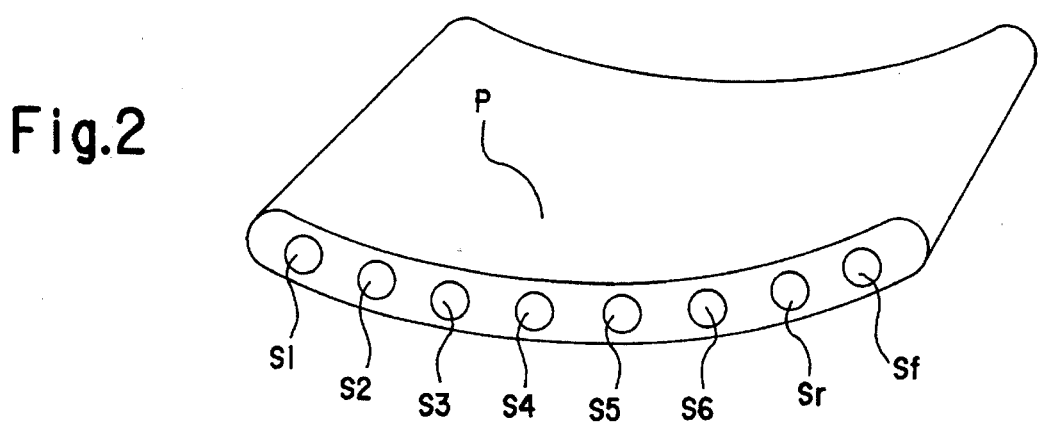
FIG. 2 is an illustration depicting a phantom to be used in accordance with the present invention.

FIG. 2 is an illustrative figure of a phantom to be used for the quantitative determination of bone mineral mass in one example in accordance with the present invention. The phantom P contains plural sample rods S1, S2, ..., produced by mixing a water equivalent material having the same X-ray transmission rate as that of water with various ratios of a standard material equivalent to bone mineral mass which has the same X-ray transmission rate as that of bone mineral mass. Among the plural sample rods being composed of a water equivalent material as the base material and having different densities of a standard material equivalent to bone mineral mass, sample rod S1 is a sample rod with the lowest density, where the density of the standard material equivalent to bone mineral mass is 0 mg/cc (namely, containing only the water equivalent material). The standard material equivalent to bone mineral mass is, for example, calcium hydroxyapatite, potassium hydrogen phosphate, calcium carbonate and the like. The phantom P also contains sample rod "Sr" of a standard material equivalent to blood, having the same X-ray transmission rate as that of blood.

Figure 1:
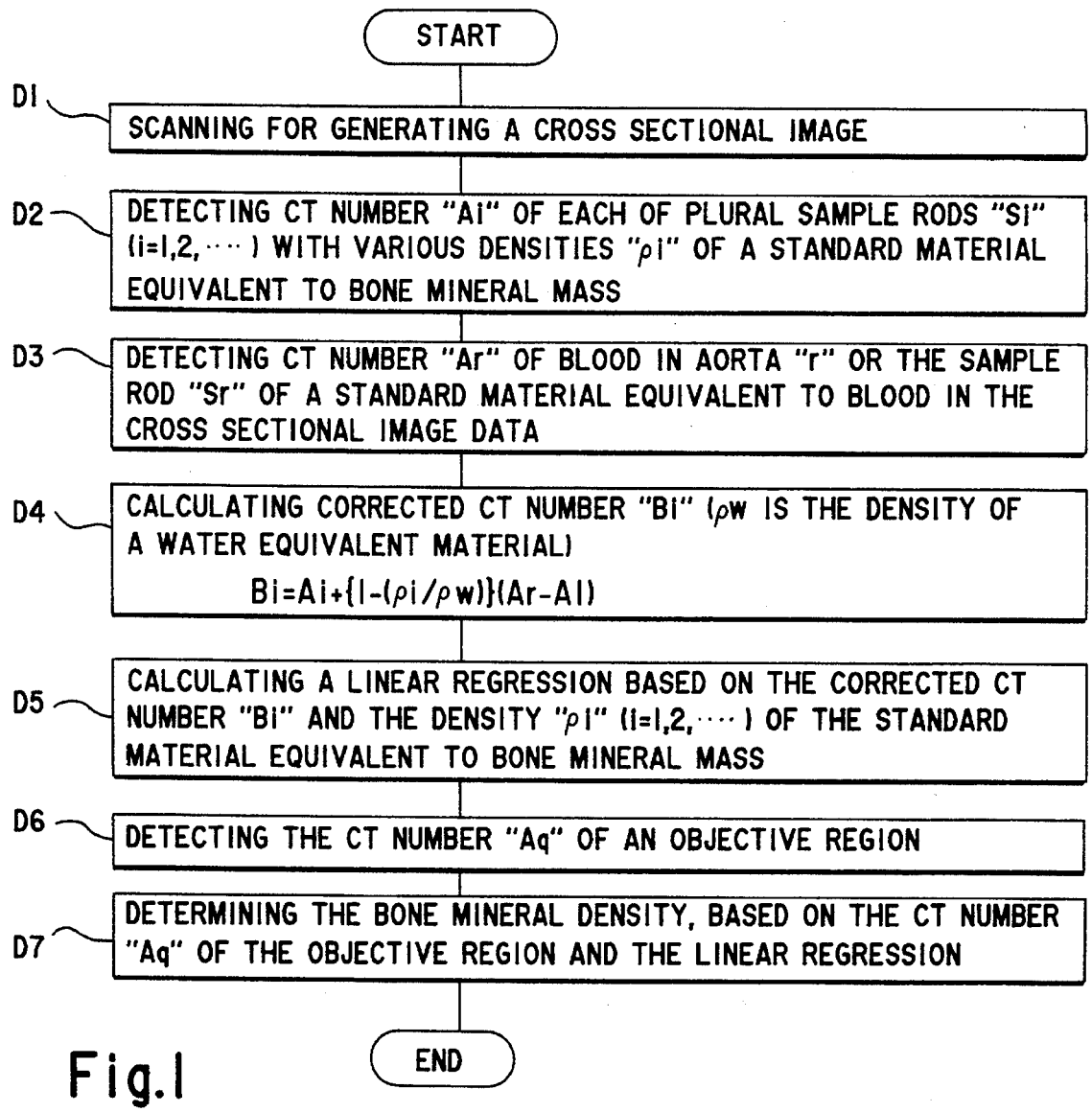
FIG. 1 is a flow chart representing the procedures of the method for quantitatively determining bone mineral mass in accordance with the present invention.

FIG. 1 is a flow chart representing the procedures of the method for quantitatively determining bone mineral mass in one example in accordance with the present invention. Following the flow chart of FIG. 1, explanation will now be made hereinbelow of a specific example where the objective region is the third lumbar vertebrae.

Phantom P is placed below the waist of subject K. Then, after an operator determines the position of the cross section including his (or her) bone marrow (for example, the third lumbar vertebrae) and the phantom P, the following procedures will be carried out when an operator directs operation unit 30 to commence the quantitative determination of bone mineral mass.

At step D1, scanning of the determined scanning cross section is effected, to obtain cross sectional image data. FIG. 3 depicts an illustrative figure of the cross sectional image from the cross sectional image data. "h" represents the image of the waist contour; and "q" represents the image of the third lumbar vertebrae. Furthermore, "r" represents the image of the aorta.

At step D2, detection is made of the CT numbers of the sample rods S1, S2, . . . having different densities of the standard material equivalent to bone mineral mass from the cross sectional image data.

At step D3, detection is made of the CT number of blood or a standard material equivalent to blood. That is to say, detection is made of the CT number "Ar" either of blood "r" in aorta or of the sample rod "Sr" of the standard material equivalent to blood in the cross sectional image data. For detecting the CT number of blood in the aorta, the sample rod "Sr" is not necessary.

At step D4, calculation is made of corrected values B1, B2, ..., of the CT numbers A1, A2, ..., on the basis of the following equation;

$$Bi=Ai+\{1-(\rho i/\rho w)\}(Ar-Al)$$

wherein "$\rho i$" is the density of the standard material equivalent to bone mineral mass in the sample rod "Si"; "$\rho w$" is the density $\rho 1$ of the water equivalent material, ie. sample rod S1; and i=1,2, ... The procedure is for calculating corrected CT number "Bi" of each CT number "Ai" of a sample, by substituting the CT number due to the water equivalent material, contained in the CT number "Ai" with the CT number of blood or the standard material equivalent to blood in the cross sectional image data obtained by scanning.

At step D5, on the basis of the corrected CT numbers B1, B2, ... from such calculation and the known densities $\rho 1$, $\rho 2$, ..., of the standard material equivalent to bone mineral mass, calculation should be done of a linear regression F:y=H+G·x, as shown in FIG. 4, representing the relation between the corrected CT number and the bone mineral density of the standard material equivalent to bone mineral mass, following the least squares method. In the figure, x axis represents bone mineral density, while y axis represents CT number. Herein, the y axial intercept "H" corresponds to CT number "Ar" within the error range, while "G" represents linear slope.

At step D6, the CT number "Aq" of the third lumbar vertebrae "q" is detected.

At step D7, the bone mineral density of the third lumbar vertebrae "q" is determined on the basis of the CT number "Aq" of the third lumbar vertebrae "q" and the linear regression "F", as follows;

$$X=(Aq-H)/G$$

From the results of the above steps D1 to D7, the shift of the bone mineral density X due to the difference in tube voltage is small, compared with the conventional method, which enables more precise determination of bone mineral density.

Figure 9:
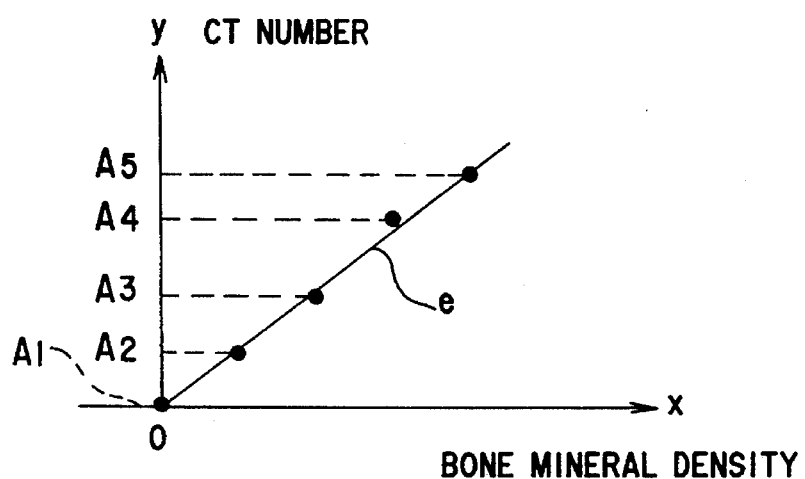
FIG. 9 is an illustration depicting a linear regression by the conventional method for quantitatively determining bone mineral mass.
Figure 10:
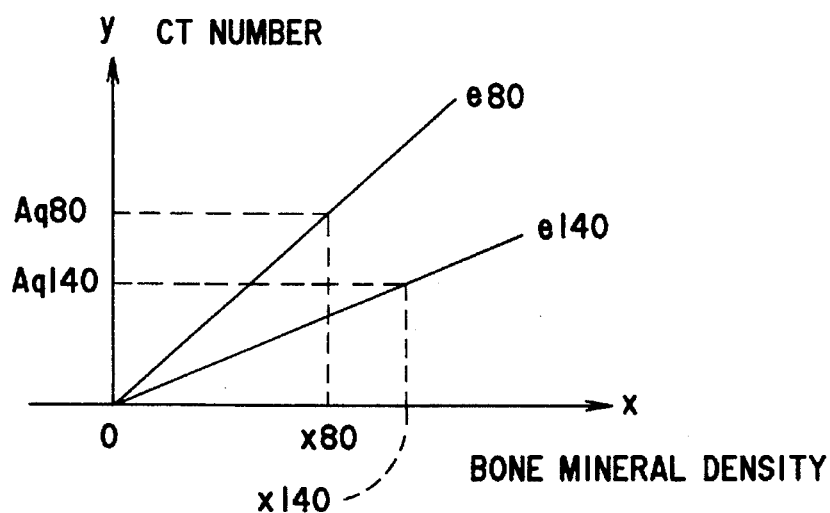
FIG. 10 is an illustration depicting linear regressions by the conventional method for quantitatively determining bone mass.
Figure 11:
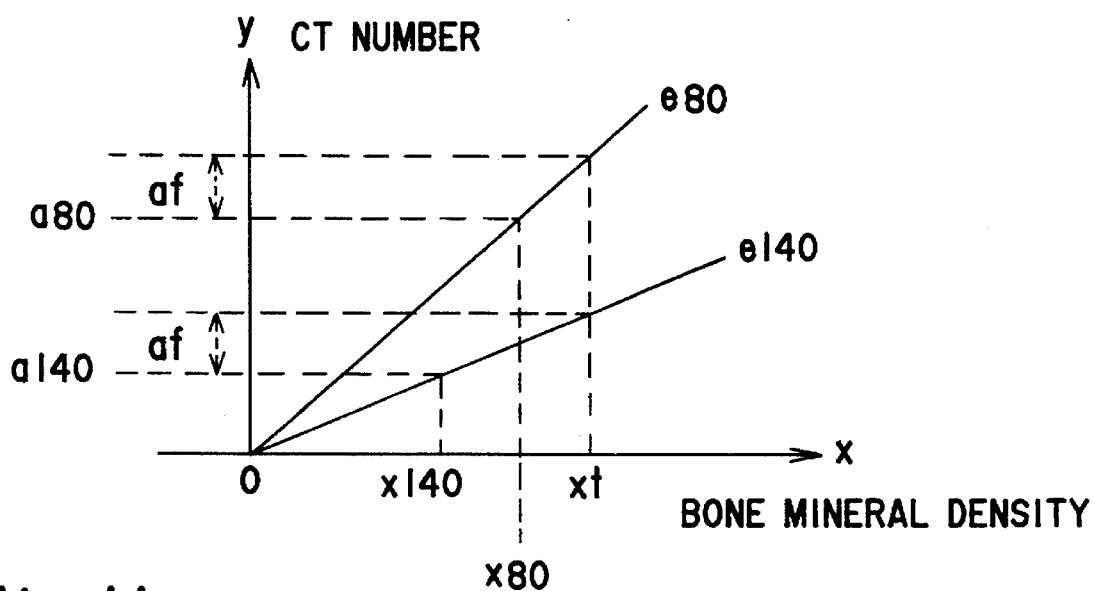
FIG. 11 is a schematic view of the error due to fat by the method for quantitatively determining bone mineral mass.

The effect will now be explained with reference to FIG. 5 showing the results of the measurements at different levels of tube voltage, ie. 80 kV and 140 kV. In the figure, "F80" is a linear regression: y=H80+G80·x, from the scanning at a tube voltage of 80 kV; "Aq80" is the CT number of the objectives region (third lumbar vertebrae "q") at the scanning; and "x80" is the bone mineral density obtained from them. Also, "F140", "Aq80" and "x140" are a linear regression y=H140+G140·x, the CT number and the bone mineral density, respectively, obtained at a tube voltage of 140 kV, wherein the sets of "H80" and "G80" and of "H140" and "G140" represent a set of y axial intercept and linear slope of the linear regressions "F80" and "F140", respectively. In the figure, linear regressions depicted in two dot chain line, "f80" and "f140", are calculated for comparison, using the CT number "Ai" of each sample as it is, without using corrected CT number "Bi" of each sample, and these correspond to the linear regressions "e80" and "e140" obtained by the conventional method (see FIG. 9).

According to the results from the steps D1 to D7, the variation of bone mineral density between "x80" and "x140" due to the difference in tube voltage is small, compared with the conventional method. As has been described above, the error is small even if the density is measured at any tube voltage, so that more precise measurement of bone mineral density is realized with correction of the error factor due to blood.

Furthermore, the order of the steps D2 and D3 may be exchanged in the above procedures, and these steps may be placed intermediately from the step D1 to the step D4. Also, the step D6 may be placed at any position from the step D1 and the step D7.

From the results described above, the bone mineral densities measured are then X80>x140. The error has an identical tendency to the shift of the CT number due to a fat factor. Therefore, by effecting the steps D1 to D6 at different two levels of tube voltage, Ej (j=1,2) and effecting the other step D70 using the two results instead of the step D7 to correct the decrease in CT number due to fat, bone mineral density can be measured with higher precision.

Figure 6:
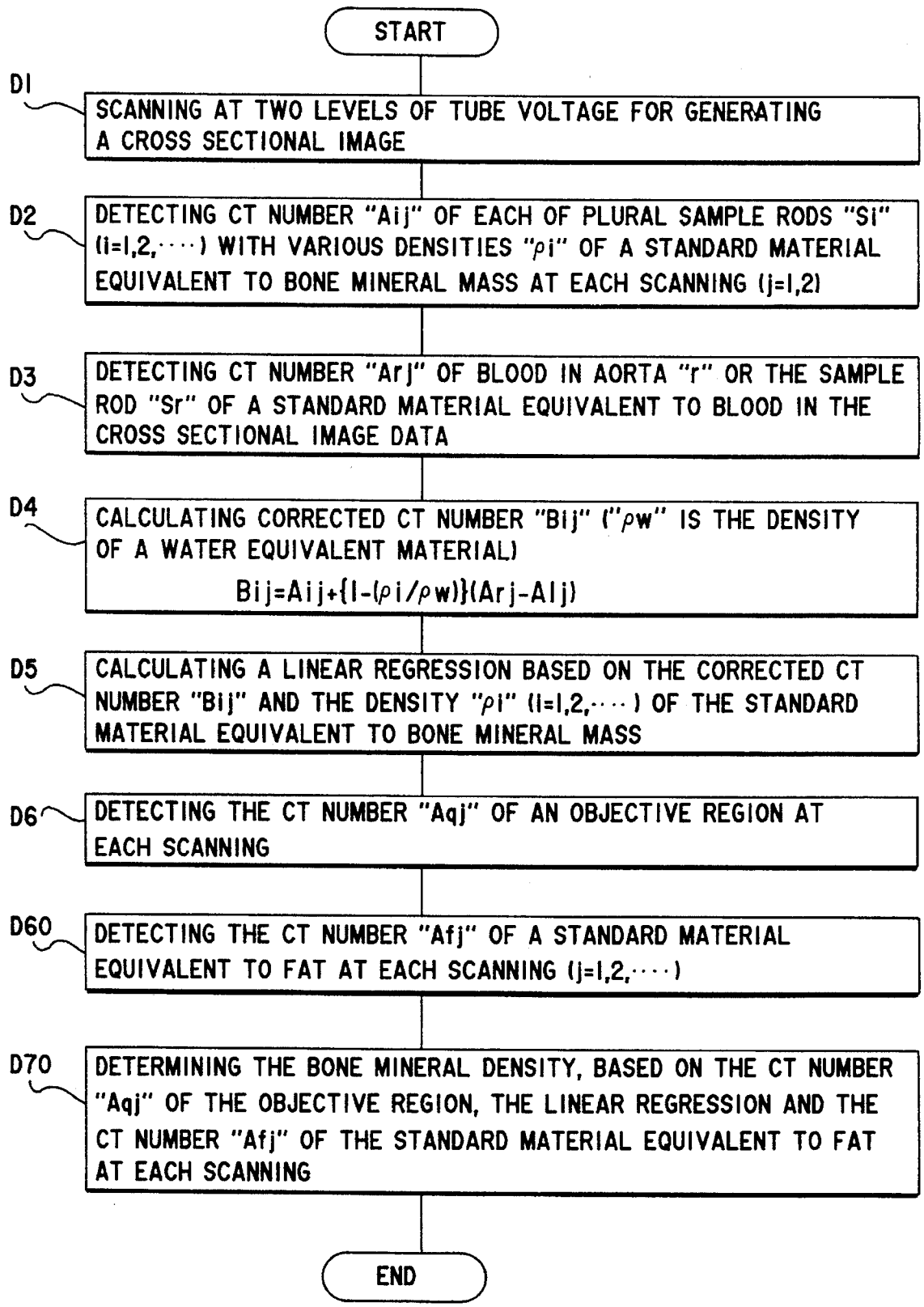
FIG. 6 is a flow chart representing the procedures of the other method in accordance with the present invention.

The detailed explanation will be made hereinbelow with reference to the flow chart in FIG. 6. In this case, phantom P contains sample rod "Sf" of a standard material equivalent to fat, in addition to the sample rods, S1, S2, ... and the sample rod "Sr" of a standard material equivalent to blood.

As has been described above, the phantom P is placed below the waist of subject K, and then, after the third lumbar vertebrae is determined as a scanning cross section, the procedure will be carried out when an operator directs operation unit 30 to commence the quantitative determination of bone mineral mass.

Step D1 is carried out at different two levels of tube voltage, ie. E1 and E2. That is, by effecting scanning of the cross section to be scanned at different two levels of tube voltage, E1 and E2, two cross sectional image data are obtained. The two levels of scanning should preferably be done at a close interval so as to decrease the positional shift of the two images.

Step D2 is effected of the two cross sectional image data. In the individual two cross sectional image data, the CT numbers of sample rods, S1, S2, S3, ..., ie. A1j, A2j, S3j, ... (j=1,2) are detected.

For the two cross sectional image data, step D3 is effected to detect the CT number of blood or a standard material equivalent to blood. That is, the CT number "Ar1" either of the aorta "r" or of the sample rod "Sr" of the standard material equivalent to blood is detected in the cross sectional image data at the tube voltage E1; in such manner, the CT number "Ar2" is detected at the tube voltage E2. When the CT number of blood in the aorta "r" is to be detected, the sample rod "Sr" of the standard material equivalent to blood is not required.

Step D4 is effected on the data based on the two levels of tube voltage. That is, the corrected CT numbers B1j, B2j, B3j, ... (j=1,2) of the CT numbers A1j, A2j, A3j, ... at a tube voltage Ej (j=1,2) are calculated as follows;

$$Bi=Ai+\{1-(\rho i/\rho w)\}(Ar-Al).$$

That is, the calculation is done on the basis of the equation;

$$Bij=Aij+\{1-(\rho i/\rho w)\}(Arj-Alj),$$

wherein "$\rho i$" represents the density of the standard material equivalent to bone mineral mass in sample rod "Si"; and "$\rho w$" represents the density $\rho 1$ of the water equivalent material, namely, sample rod S1. Herein, "i" is the number of sample rod and i=1, 2, 3, ... ; and "j" represents two levels of tube voltage and j=1,2.

Step D5 is effected on the two data sets (j=1,2). That is, based on the corrected CT numbers B1j, B2j, B3j, . . . in calculation and the known densities ρ1, ρ2, ρ3, . . . of the standard material equivalent to bone mineral mass for the two data sets, two linear regressions representing the relation between the corrected CT number and the bone mineral density of the standard material equivalent to bone mineral mass and being expressed as Fj: y=Hj+Gj·x, are calculated by the least square method and the like. Herein, "Hj" corresponds to CT number "Arj" within the error range.

Step D6 is effected on the two cross sectional images. That is, the CT numbers "Aq1" and "Aq2" of the third lumbar vertebrae "q" as the objective region in the individual images are detected.

A new step D60 is effected on the two cross sectional images. That is, for the individual images, the CT numbers "Af1" and "Af2" of the sample rod "Sf" of a standard material equivalent to fat are detected.

Then, Step D70 is effected in place of Step D7. That is, on the basis of the intercepts "H1" and "H2" and slopes "G1" and "G2" of the two linear regressions, the CT numbers "Af1" and "Af2" of the sample rod Sf of a standard material equivalent to fat in the two cross sectional images, the CT numbers "Ar1" and "Ar2" of the sample rod "Sr" either of the aorta "r" or of the standard material equivalent to blood in the two cross sectional images, and the CT numbers "Aq1" and "Aq2" of the objective region in the two cross sectional images, the bone mineral density X of the objective region is calculated with the correction of the shift due to blood or fat, as described hereinbelow.

That is, provided that the fat concentration in the objective region is defined as F, the shift of the CT number due to fat at two levels of tube voltage is expressed as follows;(Afj–Arj)F. Hence, the CT number without the fat effect should be expressed as Aqj–(Afj–Arj)F. These should independently meet the linear regression y=Hj+Gj·x, so the following equation should be established when true bone mineral density is defined as "X";

$$Aq1-(Af1-Ar1)F = H1+G1 \cdot X$$

$$Aq2-(Af2-Ar2)F = H2+G2 \cdot X.$$

Based on these equations, the bone mineral density should be represented as follows;

$$X=\{(Aq1-H1)(Af2-Ar2)-(Aq2-H2)(Af1-Ar1)\}/\{(Af2-Ar2)G1-(Af1-Ar1)G2\},$$

wherein "H1" and "H2" may be used in place of "Ar1" and "Ar2" respectively

As has been described above, in accordance with the present invention, the error factor due to blood is corrected, thereby enabling the correction of the error factor due to fat, whereby both the error factors are corrected to measure bone mineral density with higher precision.

In the forgoing example, the best mode of calculating bone mineral density has been explained under the provision that the decrease in CT number due to fat varies depending on tube voltage and the like. However, more simple calculation may be done when the shift of the CT number due to fat is defined as constant as "af".

When the shift of the CT number due to fat is defined as "af"0 the CT numbers corrected for the fat effect are (Aq1–af) and (Aq2–af), which should satisfy the two linear regressions, so that the following equation is established when true bone mineral density is defined as "X";

$$Aq1-af = H1+G1 \cdot X$$

$$Aq2-af = H2+G2 \cdot X$$

On the basis of these equations, bone mineral density is calculated as follows;

$$X=\{(Aq1-H1)-(Aq2-H2)\}/(G1-G2).$$

In this case, precision may be decreased more or less. Nevertheless, the phantom P does not require sample rod "Sf" of a standard material equivalent to fat, or step D60 is not necessary.

Furthermore, the order of the steps D2 and D3 may be exchanged in the above procedures, and these steps maybe placed intermediately from the step D1 to the step D4. Also, the order of the step D6 and the step D60 may be changed, and these steps may be interposed anywhere from the step D1 to the step D70 in any order. In the example, two levels of tube voltage are employed for the procedures at the individual steps in the example, but the steps D1 to D60 may be effected first at one tube voltage, and then, the steps D1 to D60 may be effected at another tube voltage, followed by step 70.

According to the method for quantitatively determining bone mineral mass by a CT system, in accordance with the present invention, bone mineral density is determined on the basis of the corrected CT number capable of more accurately reproducing the objective region after the correction of error factors such as blood, and therefore, measurement results are more accurate.

Still furthermore, because corrected CT numbers are determined at plural levels of tube voltage to exclude the effect of fat and the like, measurement results with greater accuracy are obtained.

What is claimed is:

1. A method for quantitatively determining bone mineral mass by a CT system, comprising scanning an objective region together with plural samples produced by mixing a water equivalent material with various ratios of a standard material equivalent to bone mineral mass and determining the bone mineral density of the objective region with reference to the CT numbers of the plural samples with various densities of the standard material equivalent to bone mineral mass, wherein corrected CT number of each of the samples with various densities of the standard material equivalent to bone mineral mass is calculated by substituting the CT number derived from the water equivalent material and contained in the CT number of each of the samples with the CT number of blood or a standard material equivalent to blood in the cross sectional image data generated from such scanning, whereby the bone mineral density of the objective region is determined on the basis of the corrected CT number of each of the samples.

2. A method for quantitatively determining bone mineral mass by a CT system, comprising scanning an objective region together with plural samples produced by mixing a water equivalent material with various ratios of a standard material equivalent to bone mineral mass and determining the bone mineral density of the objective region with reference to the CT numbers of the plural samples with various densities of the standard material equivalent to bone mineral mass, wherein by determining the CT number of each of the samples with various densities of the standard material equivalent to bone mineral mass and the CT number of blood or a standard material equivalent to blood in the cross sectional image data from scanning, calculating corrected CT number of each of the samples by substituting the CT number derived from the water equivalent material and contained in the CT number of each of the samples with the CT number of blood or the standard material equivalent to blood, and determining the relation between the density of the standard material equivalent to bone mineral mass in the samples and the corrected CT number of each of the samples, the bone mineral density of the objective region is determined from the CT number of the objective region on the basis of said relation.

3. A method for quantitatively determining bone mineral mass by a CT system, comprising scanning an objective region together with plural samples produced by mixing a water equivalent material with various ratios of a standard material equivalent to bone mineral mass and determining the bone mineral density of the objective region with reference to the CT numbers of the plural samples with various densities of the standard material equivalent to bone mineral mass, wherein by effecting multiple scanning at different levels of X-ray tube voltage, determining the CT number of each of the samples with various densities of the standard material equivalent to bone mineral mass at each scanning and the CT number of blood or a standard material equivalent to blood at each scanning, calculating corrected CT number of each of the samples by substituting the CT number derived from the water equivalent material and contained in the CT number of each of the samples at each scanning with the CT number of blood or the standard material equivalent to blood, and determining the relation at each scanning between the bone mineral density and the corrected CT number based on the densities of the standard material equivalent to bone mineral mass in the samples and the corrected CT numbers at each scanning, the bone mineral density of the objective region is determined by using the relation at each scanning and the CT number of the objective region at each scanning.

4. A method for quantitatively determining bone mineral mass by a CT system, comprising scanning an objective region together with plural samples produced by mixing a water equivalent material with various ratios of a standard material equivalent to bone mineral mass and determining the bone mineral density of the objective region with reference to the CT numbers of the plural samples with various densities of the standard material equivalent to bone mineral mass, wherein by effecting multiple scanning at different levels of X-ray tube voltage, determining the CT number of each of the samples with various densities of the standard material equivalent to bone mineral mass at each scanning, the CT number of blood or the standard material equivalent to blood at each scanning and the CT number of a standard material equivalent to fat at each scanning, calculating corrected CT number of each of the samples by substituting the CT number derived from the water equivalent material and contained in the CT number of each of the samples at each scanning with the CT number of blood or the standard material equivalent to blood, and determining the relation at each scanning between the bone mineral density and the corrected CT number based on the densities of the standard material equivalent to bone mineral mass in the samples and the corrected CT numbers at each scanning, the bone mineral density of the objective region is determined by using the relation at each scanning, the CT number of the standard material equivalent to fat at each scanning and the CT number of the objective region at each scanning.

* * * * *